United States Patent [19]

Ramirez de Agudelo et al.

[11] Patent Number: 6,019,887

[45] Date of Patent: *Feb. 1, 2000

[54] NITRILE SELECTIVE REMOVAL PROCESS

[75] Inventors: Maria M. Ramirez de Agudelo, Miranda; Julia T. Guerra, San Antonio; Douglaines L Marcano; Zaida Hernandez, both of Miranda, all of Venezuela

[73] Assignee: Intevep, S.A., Caracas, Venezuela

[ * ] Notice: This patent is subject to a terminal disclaimer.

[21] Appl. No.: 09/195,856

[22] Filed: Nov. 19, 1998

Related U.S. Application Data

[60] Continuation-in-part of application No. 09/097,554, Jun. 15, 1998, Pat. No. 5,858,211, which is a division of application No. 08/529,759, Sep. 18, 1995, Pat. No. 5,834,392.

[51] Int. Cl.[7] .......................... C10G 25/00; C10G 25/12; C07C 7/12

[52] U.S. Cl. ..................... 208/254 R; 208/299; 208/305; 585/826; 585/823

[58] Field of Search ................................ 208/254 R, 299, 208/305; 585/826, 823

[56] References Cited

U.S. PATENT DOCUMENTS 4,467,126  8/1984  Zinnen ..................................... 568/937

*Primary Examiner*—Walter D. Griffin
*Assistant Examiner*—Tam Nguyen
*Attorney, Agent, or Firm*—Bachman & LaPointe, P.C.

[57] ABSTRACT

An adsorption/desorption process for selectively removing nitriles from a hydrocarbon feedstock includes the steps of: (a) providing a hydrocarbon feedstock having a nitrile content of less than or equal to about 400 ppm; (b) providing an adsorbent for selective removal of nitrile from a hydrocarbon feedstock comprising a substantially homogeneous mixture of a cationic nonacidic zeolite and an inorganic oxide matrix, the zeolite having an accessibility index of between about 0.1 to about 0.4; (c) contacting the feedstock and the adsorbent at nitrile adsorption conditions whereby at least about 80% of the nitrile content is adsorbed by the adsorbent during contact with at least about 200 volumes of the feedstock per volume of the adsorbent so as to provide a used adsorbent having nitrile molecules adsorbed thereon; and (d) contacting the used adsorbent with a desorbent at desorption conditions so as to remove the nitrile molecules and provide a renewed adsorbent.

22 Claims, 5 Drawing Sheets

NITRILE SELECTIVE REMOVAL PROCESS

CROSS REFERENCE TO RELATED APPLICATIONS

This application is a continuation-in-part of U.S. patent application Ser. No. 09/097,554 filed Jun. 15, 1998, now U.S Pat. No. 5,858,211 which is a divisional application of U.S. patent application Ser. No. 08/529,759 filed Sep. 18, 1995, now U.S. Pat. No. 5,834,392.

BACKGROUND OF THE INVENTION

The invention relates to an adsorbent for selectively removing nitrites from a hydrocarbon feedstock, to a method for making the adsorbent, and to a process for removing nitrile from a hydrocarbon feedstock using the adsorbent.

Nitrile compounds are frequently undesirable contaminants in feedstocks which otherwise contain valuable fractions. Particularly, C4 and C5 cuts from FCC units can be useful in the preparation of oxygenates such as MTBE, ETBE, TAME and the like. However, these feedstocks typically contain nitriles and diolefins. The diolefins may typically be hydrogenated before and/or at the etherification reactor. Nitriles, however, must be removed upstream of the reactor and therefore must be removed in the presence of dienes which make the feedstock highly reactive.

Upstream nitrile removal techniques include washing, but propionitrile cannot be removed through washing. In the presence of hydrogenation catalysts, however, propionitrile is believed to undergo conversion to totally or partially hydrogenated products, which behave as basic nitrogen and rapidly poison the acid sites of the etherification catalyst. It is apparent that the need remains for a treatment for removal of nitrile compounds, especially propionitrile, wherein the agent used for removal is selective to nitrile and has longevity toward the selective removal of nitrile especially in the presence of relatively large amounts of dienes.

In addition, under adsorption conditions for treating such reactive feedstock, the adsorbent used retains the removed nitriles and other contaminants. It is desirable to provide a desorption process, which process removes the contaminants without damaging the adsorbent so that it can be returned to adsorption conditions for extended periods of time.

It is therefore the primary object of the present invention to provide a nitrile selective adsorbent which is not rapidly deactivated during use, even in the presence of dienes.

It is a further object of the present invention to provide a desorption method for removing retained contaminants from the adsorbent.

It is a still further object of the present invention to provide a suitable desorbent for removing retained contaminants from the adsorbent.

It is another object of the present invention to provide a process for treating a feedstock such as an FCC C4–C7 feedstock with a nitrile selective adsorbent according to the invention so as to effectively and selectively remove nitrile compounds wherein the adsorbent can be restored using a selective desorbent.

It is still another object of the present invention to provide a desorption process for restoring such an adsorbent to adsorption condition for extended periods of time.

Other objects and advantages will appear herein below.

SUMMARY OF THE INVENTION

In accordance with the invention, the foregoing objects and advantages are readily attained.

An adsorbent is provided according to the invention which comprises a substantially homogeneous mixture of a cationic nonacidic zeolite and an inorganic oxide matrix, said zeolite having an accessibility index of between about 0.1 and about 0.4, and said adsorbent being capable, when contacted with a hydrocarbon feedstock containing nitrile and containing dienes in an amount of at least about 1.0% by volume, of adsorbing at least about 80% of said nitrile during contact with at least about 200 volumes of said feedstock per volume of adsorbent.

A method for making the adsorbent of the present invention is provided which method comprises the steps of providing a cationic nonacidic zeolite; providing an inert inorganic oxide matrix; washing said matrix with an alkaline hydroxide so as to provide a washed matrix having neutralized surface acidity; calcining said washed matrix so as to provide a calcined matrix having reduced surface hydroxide; mixing said zeolite and said calcined matrix so as to provide a substantially homogeneous mixture; forming said substantially homogenous mixture into adsorbent elements; and calcining said adsorbent elements so as to provide said adsorbent.

A process for treating a hydrocarbon feedstock for removal of nitrile is provided which process comprises the steps of providing a hydrocarbon feedstock having a nitrile content of less than or equal to about 400 ppm; providing an adsorbent for selective removal of nitrile from a hydrocarbon feedstock comprising a substantially homogeneous mixture of a cationic nonacidic zeolite and an inorganic oxide matrix, said zeolite having an accessibility index of between about 0.1 and about 0.4; and contacting said feedstock and said adsorbent at nitrile adsorption conditions whereby at least about 80% of said nitrile content is adsorbed by said adsorbent during contact with at least about 200 volumes of said feedstock per volume of said adsorbent.

In further accordance with the invention, an adsorption/desorption process for selectively removing nitrites from a hydrocarbon feedstock is provided, which process comprises the steps of: (a) providing a hydrocarbon feedstock having a nitrile content of less than or equal to about 400 ppm; (b) providing an adsorbent for selective removal of nitriles from a hydrocarbon feedstock comprising a substantially homogeneous mixture of a cationic nonacidic zeolite and an inorganic oxide matrix, said zeolite having an accessibility index of between about 0.1 and about 0.4; (c) contacting said feedstock and said adsorbent at nitrile adsorption conditions whereby at least about 80% of said nitrile content is adsorbed by said adsorbent during contact with at least about 200 volumes of said feedstock per volume of said adsorbent so as to provide a used adsorbent having nitrile molecules adsorbed thereon; and (d) contacting said used adsorbent with a desorbent at desorption conditions so as to remove said nitrile molecules and provide a renewed adsorbent.

In the aforesaid adsorption/desorption process, it may be preferable to purge the system before contacting the adsorbent with a desorbent. After contacting with the desorbent, it may also be preferable to displace the desorbent with a suitable stream.

BRIEF DESCRIPTION OF THE DRAWINGS

A detailed description of preferred embodiments of the invention follows, with reference to the attached drawings, wherein.

DETAILED DESCRIPTION

The invention relates to an adsorbent for selectively removing nitrile from a hydrocarbon feedstock, to a method for preparing a nitrile selective adsorbent, to a process for treating a hydrocarbon feedstock with a nitrile selective adsorbent for removal of nitrile contaminants contained therein, and to an adsorption/desorption process wherein adsorbent according to the invention is used advantageously and then regenerated or restored for further use over an extended period of time.

According to the invention, a nitrile selective adsorbent is disclosed which comprises a substantially homogeneous mixture of a nonacidic cationic zeolite and an inorganic oxide matrix, preferably including a binder and being extruded or otherwise formed into a desired shape for use in hydrocarbon contacting processes. The zeolite is preferably selected so as to provide a high activity toward the adsorption of nitrile, and a low activity toward polymerization of dienes, while the matrix is preferably selected so as to have a high activity toward reversible adsorption of dienes, and a low activity toward the adsorption of nitrile. This combination of properties according to the invention provides the adsorbent with an advantageous and desirable selectivity toward the adsorption of nitrile compounds such as propionitrile when contacted with a nitrile containing feedstock, with a reduced tendency toward polymerization of dienes which can result in fouling of the adsorbent. Further, the activity of the adsorbent toward selective adsorption of nitriles is not rapidly deactivated during use and the adsorbent can be restored following a desorption process according to the invention.

The zeolite material of the adsorbent according to the invention is preferably selected from the group consisting of faujasite, mordenite, offretite, A-zeolite, erionite, L-zeolite, ST-5 zeolite, X-zeolite, Y-zeolite, and mixtures thereof. The zeolite is preferably nonacidic, and preferably is transformed or otherwise treated to contain cations selected from the group consisting of Li, Na, K, Cs, Mg, Ca, Sr, Ba and mixtures thereof, most preferably Na, K, Ba or mixtures thereof. The zeolite is also preferably selected and prepared so as to have an accessibility index, which will be defined below, of between about 0.1 and about 0.4. The accessibility index is a gauge of the relative accessibility to the active pore sites of the zeolite to nitrile compounds and to other compounds such as dienes.

The inorganic oxide matrix according to the invention is preferably selected from the group consisting of silica, alumina, kaolin, clays, ceramics and mixtures thereof. The matrix material is preferably substantially inert, may be crystalline or amorphous, and is treated according to the invention so as to have substantially no surface acidity. It is also preferable that the matrix be cost-effective and moldable.

According to the invention, the zeolite and matrix materials are preferably present in the adsorbent in a ratio by weight of zeolite to matrix of between about 100:1 to about 1:100. In this range the amount of zeolite is further selected based upon the amount and type of contaminants involved, and the surface area of the zeolite. The adsorbent preferably has a surface area of between about 100 and about 1000 $m^2/g$, most preferably between about 200 and about 600 $m^2/g$, and has an overall surface acidity of less than or equal to about 2.7 mmol/g. The adsorbent according to the invention is selective toward the adsorption of nitrile compounds and is therefore useful in the selective removal of nitrile contaminants from a nitrile containing feedstock.

As set forth above, the zeolite material of the adsorbent of the present invention preferably has an accessibility index of between about 0.1 and about 0.4. In accordance with the invention the accessibility index represents a ratio of the molecular accessibility volume of the zeolite material for 2 parallel pentadienes to the molecular accessibility volume of the zeolite for propionitrile. It has been found according to the invention that adsorbents containing zeolites having an accessibility index as set forth above are particularly effective in the selective removal of nitrile without diene polymerization as desired. The measurement of molecular accessibility is further illustrated in Example 7 set forth below.

The adsorbent of the present invention is preferably prepared as follows. A zeolite material is provided, preferably selected from the group consisting of faujasite, mordenite, offretite, A-zeolite, erionite, L-zeolite, ST-5 zeolite, X-zeolite, Y-zeolite and mixtures thereof. The zeolite is preferably nonacidic, and has been transformed or otherwise treated so as to contain cations preferably selected from the group consisting of Li, Na, K, Cs, Mg, Ca, Sr, Ba and mixtures thereof, most preferably Na, K, Ba or mixtures thereof. These cations have been found according to the invention to allow access of nitrile compounds to the active sites of the zeolite while prohibiting entry of more than one molecule such as dienes and thereby preventing the polymerization of dienes as desired in accordance with the present invention.

According to the invention, a matrix material is provided which is preferably selected from the group consisting of silica, alumina, kaolin, clays, ceramics and mixtures thereof. The matrix is advantageously treated in accordance with the invention so as to reduce the surface acidity of the matrix substantially to nil. This may preferably be accomplished by washing the matrix material with an alkaline base wash material such as an alkaline hydroxide. The matrix is preferably washed with the alkaline hydroxide so as to neutralize the surface acidity of the matrix which has been found to be desirable in providing an adsorbent having the desired activity and longevity toward the selective removal of nitrile according to the invention. According to the invention, the alkaline hydroxide wash solution is preferably selected from the group consisting of NaOH, KOH, $NH_4OH$ and mixtures thereof. After washing with the alkaline hydroxide, the matrix is preferably further washed, for example with water, so as to remove any remaining un-reacted alkaline hydroxide. The washed matrix is then preferably dried, for example overnight at a temperature of between about 80 and about 250° C., and then calcined, preferably at a temperature of between about 400 and about 850° C. so as to remove any remaining hydroxide (OH) on the surface of the matrix.

The washed and calcined matrix is then preferably mixed with the zeolite so as to provide a substantially homogeneous mixture thereof. As set forth above, the zeolite and matrix materials may preferably be provided in amounts sufficient to provide a ratio by weight of the zeolite to the matrix material of between about 100:1 and about 1:100.

Depending upon the desired form of the adsorbent end product, a binder material may preferably be added to the mixture so that the mixture can then be extruded or otherwise formed into a desirable shape or form, depending upon the type of process in which the adsorbent is to be used. A suitable binder material is Ludox™ although other binder materials may be suitable in accordance with the invention.

After extrusion, the extruded adsorbent elements are preferably dried, for example overnight at a temperature of between about 80 and about 250° C., and then calcined, preferably at a temperature of between about 400 and about 700° C., so as to provide the final adsorbent product according to the present invention.

The described method for preparing the adsorbent product according to the invention has been found to provide an adsorbent material having a desirably low surface acidity, preferably less than or equal to about 2.7 mmol/g, as measured by the amount of irreversibly adsorbed pyridine molecules on the surface of the adsorbent. The measurement of surface acidity is further described in Example 1 below. This low surface acidity has been found according to the invention to be particularly advantageous in providing an adsorbent having the desired selectivity toward adsorption of nitriles.

The adsorbent product according to the invention is especially useful in treating hydrocarbon feedstock containing up to about 400 ppm of nitrile, preferably between about 3 and about 1000 ppm as nitrogen, and at least about 1.0% dienes, preferably at least about 2.0% dienes by volume of the feedstock. A particularly desirable feedstock is an FCC etherification feed, most preferably a C4–C7 cut of such a feed, which contains nitrile and diene contaminants. The adsorbent material according to the invention has been found to have excellent selectivity and longevity toward the removal of nitrile from such feedstocks, and the desorption method for restoring the adsorbent has also been found to provide excellent restoration of the adsorbent for extended use.

The adsorbent product of the present invention may be used in a hydrocarbon contacting process as follows. A suitable feedstock is provided, as is an adsorbent according to the invention as set forth above. The feedstock and adsorbent are preferably contacted according to the invention in suitable treatment facilities, and under moderate nitrile removal conditions, most preferably at a temperature of less than or equal to about 300° C., and a pressure of less than or equal to about 500 psi. The adsorbent according to the invention has been found to be capable of adsorption of at least 80% of the nitrile contaminant of a feedstock containing in excess of about 1.0% dienes over a treatment period during which about 200 volumes of feedstock were treated per volume of adsorbent. Thus, the adsorbent according to the present invention has an excellent selectivity and longevity for use in selectively removing nitrile contaminants from feedstocks containing relatively large fractions of nitrile and diene compounds.

Typical adsorption processes utilize more than one adsorption bed in such a way that while one (or more) is used in the adsorption mode, another (or more) is switched into desorption mode, thereby avoiding contamination of the extract with removed contaminants. Adsorption processes are classified according to the method chosen for desorption or regeneration as follows:

A thermal-swing cycle is defined as one in which desorption takes place at a temperature higher than that of the adsorption step, and in which the temperature differential is the major factor causing desorption. Cooling is usually required before the adsorbent is ready for a subsequent adsorption step.

A pressure-swing cycle is one in which desorption is carried out at a lower pressure than that of the adsorption step, and in which the pressure differential is the major factor bringing about desorption.

A purge-gas-stripping cycle is one in which desorption occurs primarily through the stripping action of a purge gas that is not adsorbed. The gas reduces the partial pressure of the sorbable component in the fluid phase and thereby affects desorption.

A displacement cycle is one in which an initial adsorbate is desorbed by the action of a second sorbable fluid, which displaces all or part of the initial adsorbate. Displacement fluids may be more strongly or less strongly sorbed than the initial adsorbate.

According to the present invention, a displacement desorption step is carried out after a particular period of use, for example after processing at least about 200 volumes of feedstock per volume of adsorbent. The desorption step according to the invention restores the adsorbent through a process whereby adsorbed nitrites, dienes and other contaminant molecules are removed from the adsorbent so as to provide a renewed adsorbent for further use as discussed above. According to the invention, adsorbed contaminants are removed using a suitable desorbent stream which acts as a displacement fluid and serves to enhance the longevity of the adsorbent material. Following desorption, adsorbent according to the invention can be cyclically returned to adsorption and will provide excellent results for at least about 50 volumes of feedstock, preferably at least about 100 volumes of feedstock.

Due to the nature of the contaminants present in the treated feedstock, displacement is preferred within the scope of the present invention since displacement can be carried out in liquid phase operations at substantially constant temperature and/or pressure conditions. Displacement with a strongly sorbed material is desirable because the displacement of sorbed contaminants is rapidly achieved. However, care must be taken to remove the displacement material itself before again using the adsorbent in process conditions so as to avoid damage to the adsorbent. On the other hand, use of a displacing material which is less strongly sorbed requires additional steps such as purge gas stripping and the like which are undesirable. Preferred displacement materials or desorbents are discussed below.

According to the invention, after the adsorbent material has been used sufficiently to have appreciable build up of adsorbed contaminants such as nitriles, dienes, sulfur compounds and the like, the adsorbent is contacted with a displacing stream or desorbent under moderate desorption conditions so as to displace the adsorbed contaminant molecules. Suitable desorbents include hydrocarbons having the structure R-X, wherein R is an alkyl group, and wherein X is a composition or moiety containing at least one atom selected from the group consisting of oxygen, nitrogen, halogen and mixtures thereof, for example having an OH, O-R' or =O structure. Preferred desorbents include alcohols, ethers, ketones, alkylhalogenides, nonbasic nitrogen compounds and mixtures thereof, most preferably methanol, methyl tert butyl ether (MTBE), tert amyl methyl ether (TAME), acetone and mixtures thereof. The desorbent is preferably contacted with a used adsorbent at desorption conditions including moderate temperature, preferably less than or equal to about 300° C., and moderate pressure, preferably less than or equal to about 500 psi. According to the invention, this desorbent advantageously is capable of excellent displacement of adsorbed contaminants, but can itself be removed with a following flushing step as set forth below.

Before contacting with the desorbent, it may be desirable to purge the adsorbent with a purging stream so as to remove any non-adsorbed feedstock material such as raffinate and the like. Purging may be carried out using a liquid or gas stream which is preferably inert with respect to the adsorbent in that the stream does not interact with the adsorbent. Suitable purging streams include C1–C16 hydrocarbons, preferably paraffins, more preferably C6–C16 aromatic hydrocarbon streams.

Following the desorption step, it may be desirable according to the invention to flush the renewed adsorbent with a flushing stream which may be a liquid or gas. The flushing stream may preferably be a stream which is inert with respect to the adsorbent, for example another hydrocarbon which is suitable for removing any remaining desorbent and/or displaced contaminant molecules. Alternatively, depending upon the concentration of desorbent, the process feedstock itself may be sufficient to flush any remaining desorbent.

It should readily be appreciated that the foregoing provides an advantageous process for regenerating used adsorbent according to the invention using a desorbent stream which is effective at displacing contaminant molecules and is itself removable from the adsorbent.

It should also be appreciated that further treatment of the adsorbent may be desired in some cases, such as filtration, fractionation, and the like. These optional additional steps are well known in the art.

EXAMPLE 1

This example illustrates the measurement of surface acidity of a sodium-Y zeolite and a kaolin matrix in accordance with the invention. The surface acidity is measured by measuring the amount of irreversibly adsorbed pyridine on samples of the relevant material. The kaolin was washed with NaOH so as to reduce surface acidity in accordance with the invention. The zeolite and matrix were pretreated with pyridine at 30° C. and 100° C., and were calcined at various temperatures between about 400° C. and about 900° C., as shown in Table 1 below.

TABLE 1

| Material | Calc. Temp. (° C.) | Irreversible adsorption (mmol pyridine/g) | |
| --- | --- | --- | --- |
| | | 30° C. | 100° C. |
| Na-Y | 500 | 2.5 | 1.5 |
| | 600 | 2.7 | 1.7 |
| kaolin | 600 | 0.1 | 0.02 |
| | 800 | 0.1 | 0.0 |

As shown in Table 1, zeolite according to the invention illustrates a very weak acidity which is substantially unaffected by calcination temperature, and the matrix material after treatment according to the invention has substantially no acidity, even at very low pretreatment temperatures.

EXAMPLE 2

Figure 1:
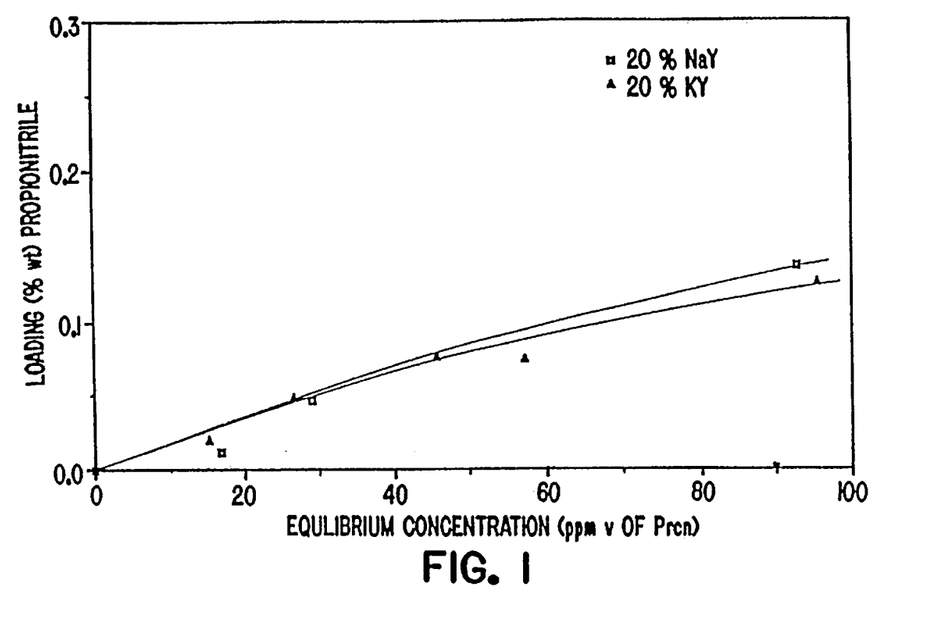
FIG. 1 is an illustration of propionitrile adsorption isotherms for Example 2.

This example illustrates the adsorption of propionitrile from test solutions using two adsorbents according to the invention. Two adsorbents were prepared according to the invention having 20% wt Na—Y zeolite in kaolin, and having 20% wt K—Y zeolite in kaolin. The samples were placed in contact with test solutions containing various concentrations of propionitrile in pentane, and were allowed to reach equilibrium. Upon reaching equilibrium, the solutions were analyzed using gas chromatography and the amount of adsorbed propionitrile was determined. FIG. 1 illustrates the adsorption isotherms for the various test solutions. As shown in FIG. 1, both adsorbents effected significant reductions in propionitrile for various loadings of the test solution. Further, the size of the cation, K or Na, did not significantly affect the adsorption of propionitrile.

EXAMPLE 3

Figure 2:
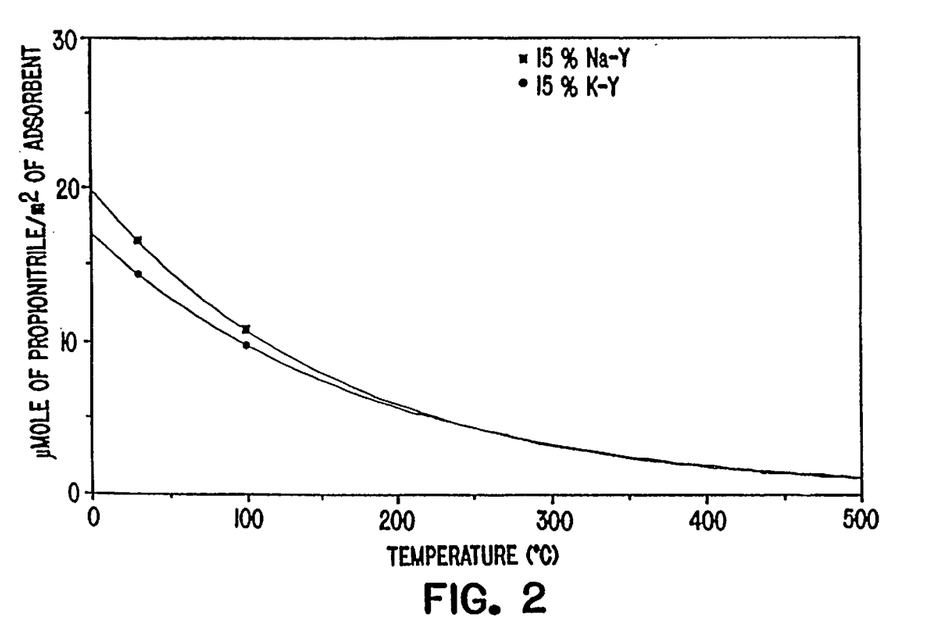
FIG. 2 is an illustration of propionitrile desorption isobars for Example 3.
Figure 3:
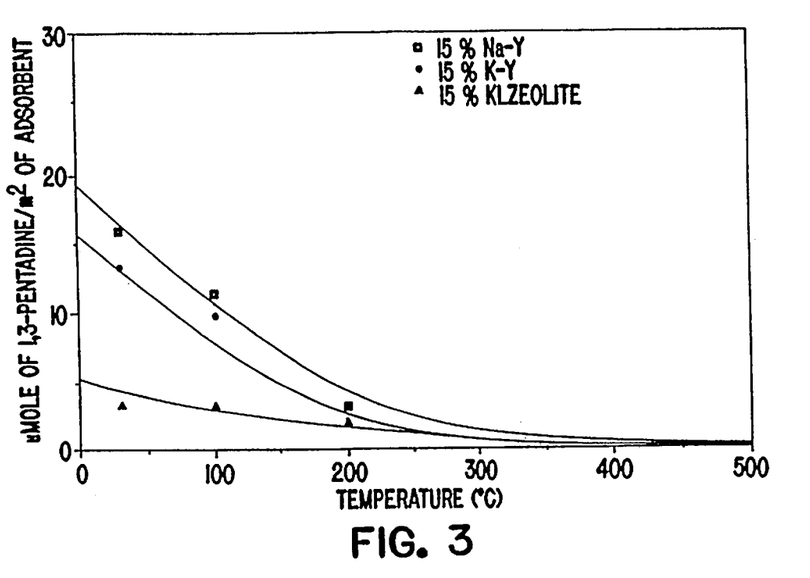
FIG. 3 is an illustration of 1,3-pentadiene desorption isobars for Example 3.

This example illustrates the desorption of nitrile and diene compounds from zeolites and matrix materials according to the invention. Two zeolite samples and a matrix sample were subjected to treatment of test solutions containing propionitrile and 1,3-pentadiene. The zeolite samples were a 15% wt Na—Y zeolite and a 15% wt K—Y zeolite, and the matrix sample was kaolin. After extended contact, these samples were regenerated using a desorption procedure at various temperatures. The propionitrile and 1,3-pentadiene desorption isobars were evaluated from the gas phase by thermogravimetric analysis at atmospheric pressure. FIGS. 2 and 3 illustrate the desorption isobars. As shown in FIG. 2, the zeolite samples exhibited an excellent desorption for propionitriles. FIG. 3 shows that the diene adsorption of the matrix is readily reversible. This example also clearly demonstrates the effect of the cation present in the zeolite in controlling the entrance of larger molecules such as the dienes into the zeolite cage. This activity of the cation serves to give the zeolite its desired selectivity toward adsorption of nitrile. Thus, certain combinations of cation and zeolite may be selected according to the invention to provide nitrile selectivity depending upon the various sizes of the nitrile, diene and cation molecules and the size of the zeolite apertures. For example, by comparing FIGS. 1 and 3, it can be seen that substituting K cations in place of Na cations does not significantly affect nitrile adsorption, but does change pentadiene adsorption, thereby increasing selectivity toward nitrile.

EXAMPLE 4

Figure 4:
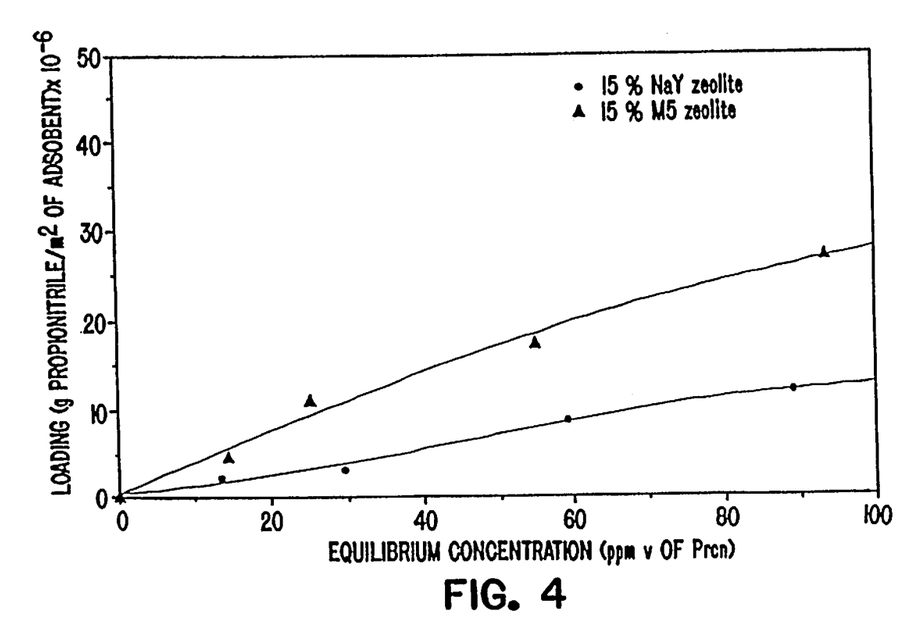
FIG. 4 is an illustration of adsorption isotherms on Na zeolites for Example 4.
Figure 5:
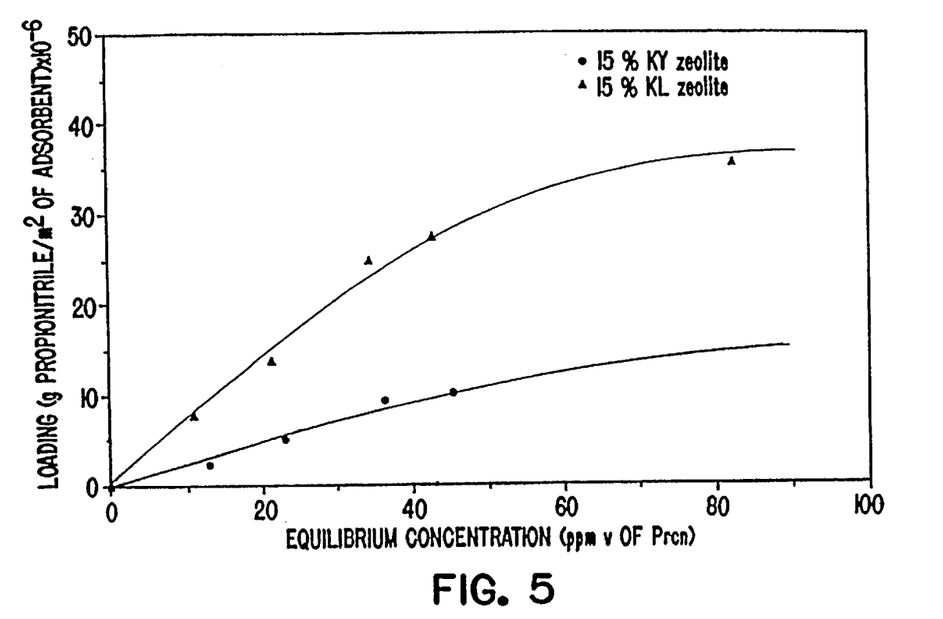
FIG. 5 is an illustration of adsorption isotherms on K zeolites for Example 4.

This example illustrates the selective adsorption of nitrile with several different zeolites. Several adsorbent samples were prepared and evaluated with test solutions as in Example 2. The samples tested were a 15% wt Na—Y zeolite in kaolin, a 15% wt Na-mordenite in kaolin, a 15% wt K—Y zeolite in kaolin, and a 15% K—L zeolite in kaolin. FIGS. 4 and 5 illustrate the adsorption isotherms for the various samples tested, and show the effect of using zeolites having different surface areas in accordance with the invention. FIG. 5 illustrates the advantage of K—Y zeolite over K—L zeolite in this application wherein K—Y zeolite adsorbs more nitrile than K—L zeolite, with a reduced adsorption of pentadiene. These examples illustrate that the proper selection of cation, zeolite and matrix in accordance with the invention can be manipulated so as to control the selectivity of the adsorbent to nitrile removal, particularly by avoiding factors that favor diene polymerization, namely bimolecular diffusion and acidity.

EXAMPLE 5

This example compares the selectivity for nitrile removal of a 40% wt. Na—Y zeolite in kaolin adsorbent extruded using Ludox™ as a binder according to the present invention, and several commercial adsorbents, namely, Selexsorb CD (0.7% diene), INTGARD-A (0.7% diene) and Selexsorb CD (<0.1% diene). The feedstock was a C5–C6 FCC cut having a composition as shown in Table 2 below.

TABLE 2

| Feedstock | Composition |
| --- | --- |
| C4 | 2.1% |
| C5 | 20.7% |
| C6 | 53.4% |
| C7 | 21.6% |
| diene | 2.0% |
| nitrile | 9.6 N ppm |
| basic nitrogen | 1.5 ppm |
| total sulfur | 244 ppm |

Figure 6:
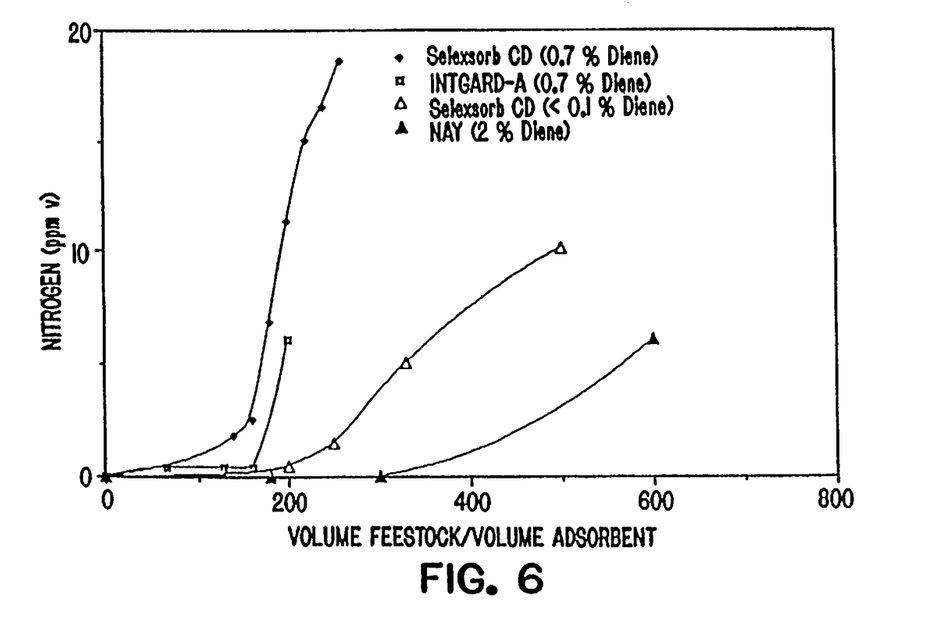
FIG. 6 is an illustration of results of the pilot plant test of Example 5.

The feedstock and the various adsorbents being tested were contacted in a pilot plant under identical conditions, and the results are set forth in FIG. 6. As shown, the adsorbent of the present invention clearly outperforms the commercial adsorbents in both selectivity and longevity with respect to nitrile removal.

EXAMPLE 6

This example illustrates the preparation of an adsorbent according to the invention. A fully exchanged Na—Y zeolite and a kaolin matrix are provided. The kaolin was washed with NaOH so as to neutralize the exeisting surface acidity of the kaolin matrix. The neutralized matrix was then washed with water until remaining un-reacted NaOH was removed. The wet washed kaolin was then dried overnight at temperatures between 80 and 250° C., and the dried kaolin was then calcined at temperatures between 400 and 850° C. until all surface OH groups were removed. The calcined kaolin was then mixed with the zeolite so as to provide a homogeneous mixture thereof, and peptized alumina was added to the mixture as a binder. The combination of mixture and peptized alumina was then extruded so as to provide adsorbent elements of the desired size and shape, and the adsorbent elements were dried overnight at temperatures between 80 and 250° C. The dried adsorbent elements were then calcined at temperatures between 400 and 700° C. to obtain the desired nitrile selective adsorbent according to the invention.

EXAMPLE 7

This example illustrates the measurement of the accessibility index for several zeolites in accordance with the invention. Three zeolites, namely Y-zeolite, mordenite and L-zeolite, were each evaluated when loaded with Na and K cations respectively. The molecular accessibility of these zeolites with respect to propionitrile, pentadiene, I(2 lineal pentadiene mol) and II(2 parallel pentadiene mol) was determined using the Catalysis™ program from Biosym Technologies Inc. The results of these measurements are set forth below in Tables 3 and 4. Both linear and parallel arrangements for the dienes were considered in order to evaluate the possibility of polymerization. The data set forth in Tables 3 and 4 illustrate that the zeolite according to the invention will adsorb more nitrile than dienes, and that the potential for diene polymerization (by getting at least two diene molecules together) is reduced.

TABLE 3

| | (# molecules per unit cell) | | | | | |
| --- | --- | --- | --- | --- | --- | --- |
| | Na-Y | K-Y | Na-Mor | K-mor | Na-L | K-L |
| propionitrile (A) | 181 | 153 | 21 | 19 | 16 | 16 |
| pentadiene | 128 | 124 | 19 | 15 | 14 | 12 |
| I(2 lineal pentadiene mol) | 54 | 53 | 10 | 10 | 9.3 | 9.7 |
| II(2 parallel pentadiene mol) (B) | 51 | 45 | 5 | 7 | 6 | 4.8 |
| Accessibility index (B/A) | 0.28 | 0.29 | 0.23 | 0.36 | 0.38 | 0.30 |

TABLE 4

| | (# molecules per g. zeolite) | | | | | |
| --- | --- | --- | --- | --- | --- | --- |
| | Na-Y | K-Y | Na-Mor | K-mor | Na-L | K-L |
| propionitrile (A) | 14.4 | 11.5 | 7 | 6.1 | 6.8 | 6.4 |
| pentadiene | 10.2 | 9.3 | 6.3 | 4.8 | 6.1 | 4.8 |
| I(2 lineal pentadiene mol) | 4.3 | 3.9 | 3.3 | 3.3 | 3.9 | 3.9 |
| II(2 parallel pentadiene mol) (B) | 4.1 | 3.4 | 1.7 | 2.3 | 2.5 | 1.9 |
| Accessibility index (B/A) | 0.28 | 0.30 | 0.24 | 0.38 | 0.37 | 0.30 |

EXAMPLE 8

A 220 cc adsorber was loaded with 160 cc of an adsorbent according to the present invention having a 40% Na-zeolite in a clay matrix. A TAME C5 cut feedstock was taken from an FCC unit. The feedstock initially contained 2% dienes and 12 ppmv propionitrile (PCN) as set forth in Table 5 below, and was doped for this example with additional PCN so as to reach a total concentration of about 123 ppmv PCN.

TABLE 5

| % C4 | 2.1 |
| --- | --- |
| % C5 | 20.7 |
| % C6 | 53.4 |
| % C7 | 21.6 |
| % Diolefins | 2.0 |
| Nitriles (N ppm) | 12.0 |
| Basic nitrogen (ppm) | 1.5 |
| Total sulfur (ppm) | 244.0 |

The adsorption conditions were a pressure of 50 psig, Temperature of 25° C., nitriles content of 123 ppmv, LHSV of 2 $h^{-1}$ and process time of 12 h.

Figure 7:
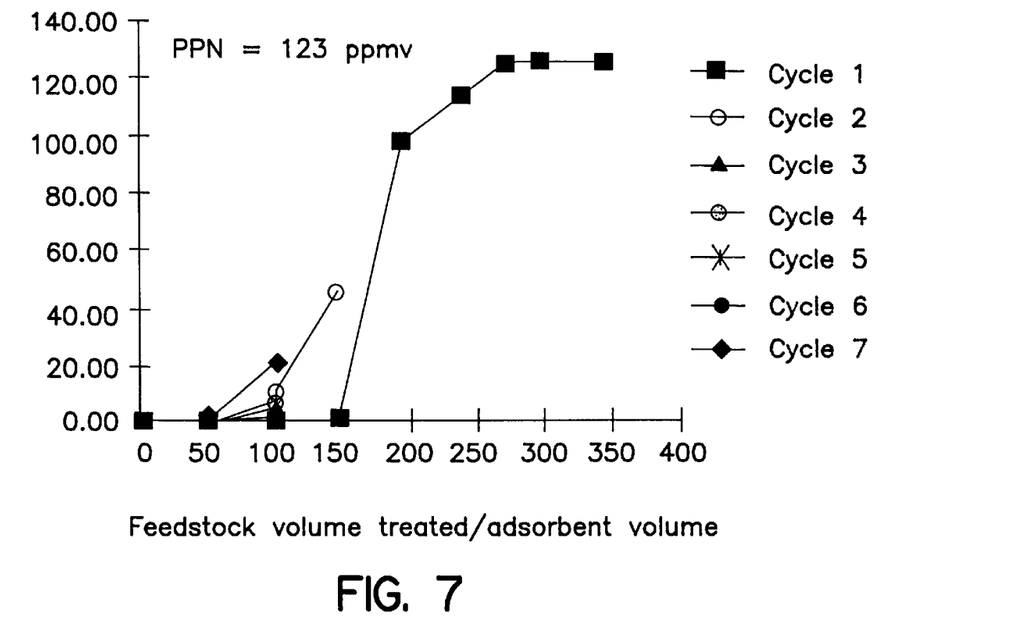
FIG. 7 is an illustration of breakthrough curves for a 2% dienes and PCN=123 ppmv feedstock as discussed in Example 8.

A desorption stage was then carried out using a C5 stream for purging, methanol for displacement and C5 for flushing after the displacement. The desorption was carried out at a pressure of 50 psig, and a temperature of 250° C. During the purging stage, 24 volumes per adsorbent volume were used at an LHSV of 3 $h^{-1}$ for a period of 8 h, followed by displacement using 6 volumes per adsorbent volume at an LHSV of 3 $h^{-1}$ for a period of 2 h. The renewed adsorbent was then flushed using 6 volumes per adsorbent volume at an LHSV of 3 $h^{-1}$ for a period of 2 h. The results are set forth in FIG. 7. A shown, the desorption process of the present invention restores the adsorbent for use in a steady nitrile removal cyclic operation, with each cycle providing excellent results for at least about 50 volumes of feedstock per volume of restored adsorbent.

EXAMPLE 9

This example demonstrates the regeneration capacity of two different desorbent materials following the adsorption/ desorption procedure as set forth in Example 8 above. Two cycles were carried out following regeneration using desorbent 1 which was methanol in accordance with the present invention, and using desorbent 2 which was pentane. The results of these two cycles for each of desorbent 1 and desorbent 2 are set forth in FIGS. 8 and 9 respectively.

Figure 8:
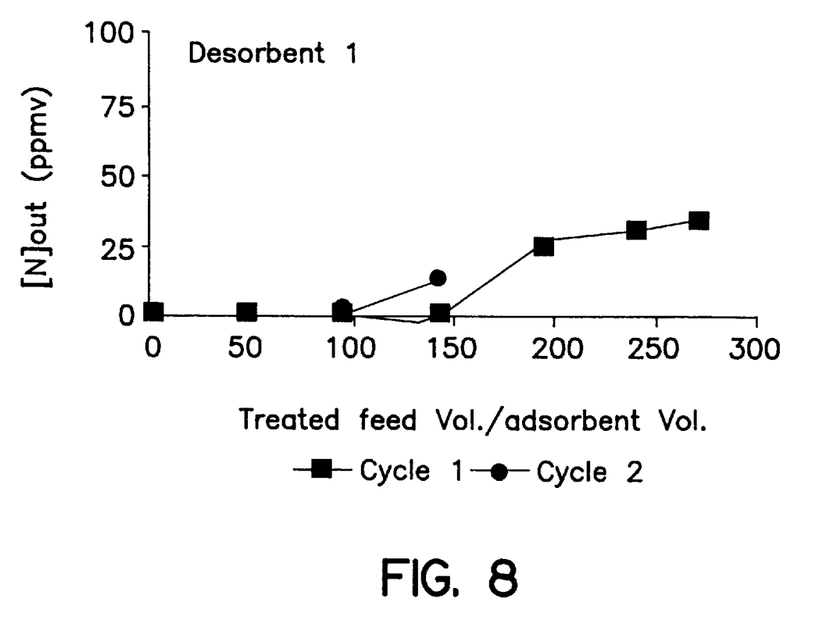
FIG. 8 illustrates regeneration capacity using methanol according to the invention.
Figure 9:
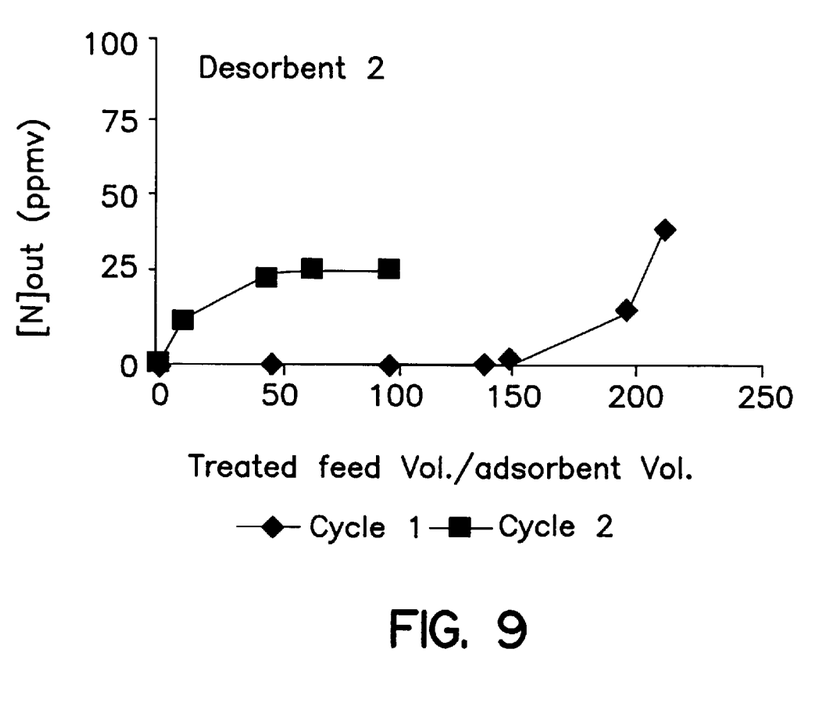
FIG. 9 illustrates regeneration capacity using pentane.

As shown in FIG. 8, cycles 1 and 2 following use of methanol as desorbent showed excellent results, with a steady increase of nitriles in the product stream in cycle 1 after about 150 volumes of feedstock per adsorbent volume, and a steady increase in cycle 2 after about 100 volumes. Referring to FIG. 9, however, cycle 1 following treatment with pentane showed a more drastic increase after about 150 volumes per volume of adsorbent, and cycle 2 showed an almost immediate increase.

It is believed that the use of methanol in accordance with the present invention as a desorbent is more affective because the methanol provides for a chemical displacement of nitrile, diene and other contaminants from the adsorbent, while pentane acts as a purging compound, with non-chemical displacement capacity.

Thus disclosed is an adsorbent, a method for preparing an adsorbent, a process for using the adsorbent for selective removal of nitrile from a nitrile containing feedstock, and a desorption process for restoring the adsorbent, wherein the adsorbent has an excellent selectivity and longevity toward the removal of nitrile compounds even in the presence of relatively large amounts of dienes.

It should also be noted that the characteristics of the adsorbent of the present invention are also well suited to use of the adsorbent as a catalyst support.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An adsorption/desorption process for selectively removing nitrites from a hydrocarbon feedstock, comprising the steps of:
   (a) providing a hydrocarbon feedstock having a nitrile content of less than or equal to about 400 ppm;
   (b) providing an adsorbent for selective removal of nitrites from a hydrocarbon feedstock comprising a substantially homogeneous mixture of a cationic nonacidic zeolite and an inorganic oxide matrix, said zeolite having an accessibility index of between about 0.1 and about 0.4;
   (c) contacting said feedstock and said adsorbent at nitrile adsorption conditions whereby at least about 80% of said nitrile content is adsorbed by said adsorbent during contact with at least about 200 volumes of said feedstock per volume of said adsorbent so as to provide a used adsorbent having nitrile molecules adsorbed thereon; and
   (d) contacting said used adsorbent with a desorbent at desorption conditions so as to remove said nitrile molecules and provide a renewed adsorbent.

2. A process according to claim 1, wherein said desorbent is an R—X hydrocarbon, wherein R is an alkyl group, and wherein X is a composition containing at least one atom selected from the group consisting of oxygen, nitrogen, halogen and mixtures thereof.

3. A process according to claim 2, wherein said desorbent is selected from the group consisting of alcohols, ethers, ketones, alkylhalogenides, nonbasic nitrogen compounds and mixtures thereof.

4. A process according to claim 1, wherein said desorbent is selected from the group consisting of methanol, methyl tert butyl ether (MTBE), tert amyl methyl ether (TAME), acetone and mixtures thereof.

5. A process according to claim 1, wherein said desorption conditions comprise a temperature of less than or equal to about 300° C. and a pressure of less than or equal to about 500 psi.

6. A process according to claim 1, further comprising the step of, before step (d), purging said used adsorbent with a purging stream which is inert relative to said adsorbent so as to remove non-adsorbed feedstock portions from said used adsorbent.

7. A process according to claim 6, wherein said purging stream is selected from the group consisting of C1–C16 hydrocarbons.

8. A process according to claim 7, wherein said C1–C16 hydrocarbons are paraffinic hydrocarbons.

9. A process according to claim 6, wherein said purging stream is selected from the group consisting of C6–C16 aromatic hydrocarbons.

10. A process according to claim 6, wherein said purging stream is selected from the group consisting of liquid streams, gas streams and mixtures thereof.

11. A process according to claim 1, further comprising the step of flushing said renewed adsorbent with a flushing stream so as to remove said desorbent from said renewed adsorbent.

12. A process according to claim 11, wherein said flushing stream comprises a stream which is inert relative to said renewed adsorbent.

13. A process according to claim 11, wherein said flushing stream is said feedstock.

14. A process according to claim 6, further comprising the step of flushing said renewed adsorbent with a flushing stream so as to remove said desorbent from said renewed adsorbent.

15. A process according to claim 14, wherein said flushing stream comprises a stream which is inert relative to said renewed adsorbent.

16. A process according to claim 14, wherein said flushing stream is said feedstock.

17. A process according to claim 1, further comprising the step of repeating said step (c) using said renewed adsorbent whereby at least about 80% of said nitrile content is adsorbed by said renewed adsorbent during contact with at least about 50 volumes of said feedstock per volume of said renewed adsorbent.

18. A process according to claim 17, wherein at least about 80% of said nitrile content is adsorbed by said renewed adsorbent during contact with at least about 100 volumes of said feedstock per volume of said renewed adsorbent.

19. A process according to claim 1, wherein said feedstock further has a diene content of at least about 1.0% by volume of said feedstock.

20. A process according to claim 19, wherein said diene content is at least about 2.0% by volume of said feedstock.

21. A process according to claim 1, wherein said feedstock is an FCC etherification feed.

22. A process according to claim 21, wherelin said feedstock is a C4–C7 cut of said FCC etherification feed.

* * * * *

UNITED STATES PATENT AND TRADEMARK OFFICE
CERTIFICATE OF CORRECTION

PATENT NO. : 6,019,887
DATED : February 1, 2000
INVENTOR(S) : Maria M. Ramirez de Agudelo et al.

It is certified that error appears in the above-identified patent and that said Letters Patent is hereby corrected as shown below:

On the title page,

1. Column 1, line 13 (2nd line under BACKGROUND OF THE INVENTION), "nitrites" should be corrected to --nitriles--.
2. Column 2, line 37 "nitrites" should be corrected to --nitriles--.
3. Column 4, line 67 "(OH)" should be corrected to --(OH$^-$)--.
4. Column 6, line 29 "nitrites" should be corrected to --nitriles--.
5. Column 9, line 33 "exeisting" should be corrected to --existing--.
6. Column 10, line 53 "250°C" should be corrected to --25°C--.

IN THE CLAIMS:

1. Claim 22, line 64 of column 12, "wherelin" should be corrected to --wherein--.

Signed and Sealed this

Twenty-ninth Day of May, 2001

Attest:

NICHOLAS P. GODICI

Attesting Officer

Acting Director of the United States Patent and Trademark Office